United States Patent
Petereit et al.

(10) Patent No.: US 7,553,918 B2
(45) Date of Patent: Jun. 30, 2009

(54) PH-SENSITIVE POLYMER

(75) Inventors: Hans-Ulrich Petereit, Darmstadt (DE);
Christian Meier, Darmstadt (DE);
Klaus Schultes, Wiesbaden (DE);
Marie-Andree Yessine, Montreal (CA);
Jean-Christophe Leroux, Montreal (CA)

(73) Assignees: Roehm GmbH & Co. KG, Darmstadt (DE); Universite de Montreal, Montreal (CA)

( * ) Notice: Subject to any disclaimer, the term of this patent is extended or adjusted under 35 U.S.C. 154(b) by 0 days.

(21) Appl. No.: 10/510,371

(22) PCT Filed: Oct. 22, 2002

(86) PCT No.: PCT/EP02/11791

§ 371 (c)(1),
(2), (4) Date: Oct. 5, 2004

(87) PCT Pub. No.: WO03/092732

PCT Pub. Date: Nov. 13, 2003

(65) Prior Publication Data

US 2005/0154165 A1 Jul. 14, 2005

(30) Foreign Application Priority Data

Apr. 30, 2002 (DE) .................. 102 19 505
May 7, 2002 (DE) .................. 102 20 470

(51) Int. Cl.
*C08F 20/06* (2006.01)
(52) U.S. Cl. ............... 526/317.1; 526/319; 526/328; 524/458; 524/800; 524/823; 524/831; 524/832
(58) Field of Classification Search ........... 526/319, 526/317.1, 328; 524/458, 800, 823, 831, 524/832
See application file for complete search history.

(56) References Cited

U.S. PATENT DOCUMENTS

| | | | | |
|---|---|---|---|---|
| 4,705,695 A | * | 11/1987 | Lehmann et al. | ......... 427/2.17 |
| 5,342,646 A | * | 8/1994 | Kleese et al. | ............ 427/2.1 |
| 5,548,033 A | | 8/1996 | Vetter et al. | |
| 5,644,011 A | * | 7/1997 | Lehmann et al. | ......... 526/319 |
| 5,705,189 A | * | 1/1998 | Lehmann et al. | ......... 424/451 |
| 5,730,999 A | * | 3/1998 | Lehmann et al. | ......... 424/443 |
| 5,804,632 A | * | 9/1998 | Haddleton et al. | ....... 524/458 |
| 5,837,780 A | | 11/1998 | Albrecht et al. | |
| 5,993,849 A | | 11/1999 | Assmus et al. | |
| 6,040,387 A | | 3/2000 | Albrecht et al. | |
| 6,063,399 A | | 5/2000 | Assmus et al. | |
| 6,225,401 B1 | * | 5/2001 | Rehmer et al. | ............ 524/800 |
| 6,287,470 B1 | | 9/2001 | Vetter et al. | |
| 6,555,195 B1 | | 4/2003 | Zietek et al. | |
| 6,576,255 B1 | | 6/2003 | Petereit et al. | |
| 6,624,210 B1 | * | 9/2003 | Petereit et al. | ............ 523/102 |
| 6,632,454 B2 | | 10/2003 | Beckert et al. | |
| 6,803,416 B2 | | 10/2004 | Schultes et al. | |
| 6,878,387 B1 | | 4/2005 | Petereit et al. | |
| 6,897,205 B2 | | 5/2005 | Beckert et al. | |
| 6,998,140 B2 | | 2/2006 | Meier et al. | |
| 2001/0022972 A1 | * | 9/2001 | Chittamuru et al. | ....... 424/439 |
| 2001/0055619 A1 | * | 12/2001 | Petereit et al. | ............ 424/490 |
| 2002/0160042 A1 | | 10/2002 | Petereit et al. | |
| 2003/0060381 A1 | * | 3/2003 | Meier et al. | ............ 510/141 |
| 2004/0104501 A1 | | 6/2004 | Petereit et al. | |
| 2005/0019381 A1 | | 1/2005 | Petereit et al. | |
| 2005/0079216 A1 | | 4/2005 | Petereit et al. | |
| 2005/0089571 A1 | | 4/2005 | Beckert et al. | |
| 2005/0152977 A1 | | 7/2005 | Petereit et al. | |
| 2005/0154165 A1 | | 7/2005 | Petereit et al. | |

FOREIGN PATENT DOCUMENTS

| | | |
|---|---|---|
| EP | 0 857 475 | 8/1998 |
| JP | 02-242807 | 9/1990 |
| JP | 08-81392 | 3/1996 |
| JP | 09-501457 | 2/1997 |
| WO | 99 34831 | 7/1999 |

OTHER PUBLICATIONS

.Kirk R, Othmer D, Encyclopedia of Chemical Technology, vol. 1, pp. 296 et seq., J. Wiley, New York, 1978.*
U.S. Appl. No. 09/515,098, filed Feb. 29, 2000, Assmus, et al.
U.S. Appl. No. 09/868,644, filed Jun. 28, 2001, Hoess, et al.
U.S. Appl. No. 10/532,831, filed Apr. 26, 2005, Petereit, et al.
Murthy, Niren et al. "The design and synthesis of polymers for eukaryotic membrane disruption", Journal of Controlled Release, vol. 61, pp. 137-143 1999.

* cited by examiner

*Primary Examiner*—Ling-Siu Choi
*Assistant Examiner*—Michael M Bernshteyn
(74) *Attorney, Agent, or Firm*—Oblon, Spivak, McClelland, Maier & Neustadt, P.C

(57) ABSTRACT

The invention relates to a pH-sensitive polymer which is a (meth)acrylate copolymer composed of 20 to 65% by weight acrylic and/or methacrylic acid units and 80 to 35% by weight units of $C_1$- to $C_{18}$-alkyl esters of (meth)acrylic acid, characterized in that it has a molecular weight in the range from 1 000 to 50 000 g/mol, and brings about at least 60% haemolysis at pH 5.5, and less than 5% haemolysis at pH 7.4, in a concentration of 150 µg/ml in a cytotoxicity test with human red blood cells. The invention further relates to the use of the pH-sensitive polymer as carrier for pharmaceutically effective biomolecules or active pharmaceutical ingredients and as ingredient of corresponding dosage forms.

17 Claims, No Drawings

PH-SENSITIVE POLYMER

The invention relates to a pH-sensitive polymer which has cytotoxic or membranolytic properties at pH values below pH 6.5 and which can be used as carrier for natural or synthetic biomolecules or active pharmaceutical ingredients.

PRIOR ART

Polymers which respond to stimuli have increased in importance in recent years. Corresponding polymers display modified properties after exposure to a chemical or physical influence such as, for example, to mention only a few, temperature, solvent or pH. There is particular interest in this connection in pH-sensitive polymers. Thus, for example, carboxyl group-containing polymers which form hydrophilic coil structures at high pH may be converted at low pH values into hydrophobic globule structures (see, for example, (1)).

Research is focused on pH-sensitive polymers in connection with the administration of medicinal substances. Many physiological and pathological processes such as endocytosis, tumour growth and inflammations are associated with a change in pH conditions. Examples of pH-sensitive polymers being investigated in connection with the administration of medicinal substances are, for example, α-alkylacrylic acids such as poly(2-ethylacrylic acid) and poly(propylacrylic acid) (see 2), poly(amido amines) (see 3, 4) and poly(ethylenimine), poly(L-lysine isophthalamide) (see (5)). The conformational changes induced by pH shifts influence the interactions of polymer and cell membranes in such a way that destabilization may occur. It is possible to employ, complex or conjugate pH-sensitive polymers as means for transporting with a large number of natural or synthetic biomolecules. They can be complexed or conjugated with lipids (see 6, 7, 8, 14), proteins and peptides (see 9, 10), DNA (4, 11), immunotoxins (12), antibodies (13) and/or active ingredients (3).

LIST OF THE LITERATURE CITED ABOVE

1. M. Watanabe, Y. Kosaka, K. Sanui, N. Ogata, K. Ogushi, and T. Yoden. On the mechanism of polyelectrolyte-induced structural reorganization in thin molecular films. *Macromolecules*, 20: 454-456 (1987).
2. N. Murthy, J. R. Robichaud, D. A. Tirrell, P. S. Stayton, and S. Hoffmann. The design and synthesis of polymers for eukaryotic membrane disruption. *J. Controlled Release*, 61: 137-143 (1999).
3. R. Duncan, P. Ferruti, D. Sgouras, A. Tuboku-Metzger, E. Ranucci, and F. Bignotti. A polymer-Triton X-100 conjugate capable of pH-dependent red blood cell lysis: A model system illustrating the possibility of drug delivery within acidic intracellular compartments. *J. Drug Targeting*, 2: 341-347 (1994).
4. S. C. Richardson, N. G. Pattrick, Y. K. Stella Man, P. Ferruti, and R. Duncan. Poly(amidoamine)s as potential nonviral vectors: ability to form interpolyelectrolyte complexes and to mediate transfection in vitro. *Biomacromolecules*, in press (2001).
5. M. E. Eccleston, M. Kuiper, F. M. Gilchrist, and N. K. H. Slater. pH-responsive pseudo-peptides for cell membrane disruption. *J. Controlled Release*, 69: 297-307 (2000).
6. T. Chen, L. S. Choi, S. Einstein, M. A. Klippenstein, P. Scherrer, and P. R. Cullis. Proton-induced permeability and fusion of large unilamellar vesicles by covalently conjugated poly(2-ethylacrylic acid). *J. Liposome Res.*, 9: 387-405 (1999).
7. J. L. Thomas and D. A. Tirrell. Polyelectrolyte-sensitized phospholipid vesicles. *Acc. Chem. Res.* 35: 336-342 (1992).
8. X. Guo and F. C. Szoka Jr. Steric stabilization of fusogenic liposomes by a low-pH sensitive PEG-diortho ester-lipid conjugate. *Bioconjugate Chem.*, 12: 291-300 (2001).
9. C. A. Lackey, N. Murthy, O. W. Press, D. A. Tirrell, A. S. Hoffmann, and P. S. Stayton. Hemolytic activity of pH-responsive polymer-streptavidin bioconjugates. *Bioconjugate Chem.*, 10: 401-405 (1999).
10. V. Bulmus, Z. Ding, C. J. Long, P. S. Stayton, and A. S. Hoffman. Site-specific polymer-streptavidin bioconjugate for pH-controlled binding and triggered release of biotin. *Bioconjugate Chem.*, 11: 78-83 (2000).
11. P. S. Stayton, N. Murthy, C. Lackey, C. Cheung, R. To, O. Press, and A. S. Hoffman. Bioinspired polymers designed to enhance intracellular delivery of biotherapeutics. *Proceed. Intern. Symp. Control. Rel. Bioact. Mater.*, 27: 7330 (2000).
12. C. A. Lackey, N. Murthy, P. S. Stayton, O. W. Press, A. S. Hoffman, and D. A. Tirrell. Enhancement of endosomal release and toxic activity of ricin A chain by a pH-sensitive polymer. *Proceed. Intern. Symp. Control. Rel. Bioact. Mater.*, 26: 815-816 (1999).
13. C. A. Lackey, O. W. Press, A. S. Hoffman, and P. S. Stayton. pH-sensitive polymer-protein complexes for control of intracellular trafficking of biomolecular therapeutics. *Polym. Mater. Sci. Eng.*, 84 (2001).
14. K. M. Eum, K. H. Langley, and D. A. Tirrell. Quasi-elastic and electrophoretic light scattering studies of the reorganization of dioleoylphosphatidylcholine vesicle membranes by poly(2-ethylacrylic acid). *Macromolecules*, 22: 2755-2760. (1989).

WO 97/09068 describes interactive molecular conjugates. These are in particular molecules which respond to a stimulus and which have the ability to bind to a cellular target region, the stimulus in turn influencing the binding ability. The stimulus may be given by the temperature, pH, particular ions or ionic strengths, electric fields or solvents.

A molecule which responds to a stimulus may be, for example, a pH-sensitive polymer which is combined with a molecule-which binds to a ligand, e.g. an antigen, an antibody or an active pharmaceutical ingredient. The molecular conjugate is able to respond to altered environmental conditions, e.g. to alteration of the pH from values above pH 7.0 in the region of extracellular body fluids, e.g. in the blood stream, to values below pH 6.5, which is associated with uptake into living cells, e.g. by endocytosis.

The polymers generally mentioned are based on vinyl-type monomers which have undergone free-radical polymerization and have molecular weights in the range from 1 000 to 30 000. Polymers with reactive side groups, e.g. —OH, —COOH or, preferably, —NH$_2$, are suggested for coupling proteins or peptides.

(Meth)acrylate copolymers composed of methacrylic acid units and comonomers such as C$_1$- to C$_{12}$-alkyl esters of (meth)acrylic acid are known in principle and are used in particular as coating agents and binders for drug forms.

Known examples are copolymers composed of 50% by weight methacrylic acid and 50% by weight methyl methacrylate (EUDRAGIT® L), of 50% by weight methacrylic acid and 50% by weight ethyl acrylate (EUDRAGIT® L100-55), of 30% by weight methacrylic acid and 70% by weight methyl methactylate (EUDRAGIT® S). The commercially available copolymers have molecular weights in the region of about 200 000 g/mol.

US 2001/0007666 A1 describes a composition used to increase the transport or release of substances through cell membranes, between cells, cell compartments or lipid membranes. The composition consists of a membrane transport agent which may inter alia be a pH-sensitive polymer, and physical means to increase the efficiency of the membrane transport agent, e.g. ultrasonic treatment. Particularly suitable pH-sensitive polymers are carboxyl group-containing polymers, e.g. those containing more than 50% monomer residues with carboxyl is groups. A specific example mentioned is poly(2-ethylacrylic acid) with an average molecular weight of 62 000. 50:50 copolymers of acrylic acid with ethyl, propyl and butyl acrylates are also described. Preparation is stated to be by bulk polymerization in the presence of an AIBN initiator. Molecular weight regulators are not mentioned. Since the copolymers are moreover purified by ether precipitation, the molecular weights must be assumed to be high. Even in low concentrations of a few µg, the copolymers lyse erythocytes extensively at pH 5.5 and to a smaller extent at pH 7.4 at least.

Problem and Solution

The introduction of biomolecules or active pharmaceutical ingredients into the cytoplasm and from there possibly into the cell nucleus via endosomes requires membrane-destabilizing (membrane-destroying) agents which prevent the substances traffic to (entering) the lysosomes, where they may be chemically degraded or inactivated. The polymers of interest therefore lead to destabilizing (destruction) of cell membranes at slightly acidic pH values around pH 6.5 or below, as prevail in the endosomes, but are substantially devoid of (have no) membranolytic effect at physiological pH values around pH 7.4, as occur outside the cells. The acrylic acid/alkyl acrylate copolymers of US 2001/0007666 A1 have the disadvantage that they may lead even in extremely low concentrations to cytolysis. This makes dosage thereof critical. An additional disadvantage is that some haemolysis may occur even at pH 7.4, so that the described copolymers are overall difficult to control and, if they are used in extremely small amounts, only low loading with biomolecules or active pharmaceutical ingredients is made possible. An additional disadvantage is that following parenteral administration, they might accumulate in the body. When the molecular weight of a polymer is too high, for example 62,000, excretion by glomerular filtration is prevented.

In connection with the development of drug forms intended to display their effects specifically in particular cell types, therefore, there is a continuing need for suitable polymeric carrier molecules. The intention was to develop pH-sensitive polymers which display cytotoxic or membranolytic properties only in high concentrations, or not at all, in the region of pH 7.0 or slightly higher, but have cytotoxic, or haemolytic or membranolytic effects even in low concentration in vivo below pH 6.5. The polymers are intended to be suitable as carriers (complexes and conjugates) for natural or synthetic biomolecules or active pharmaceutical ingredients which are to be released inside cells via uptake into endosomes and subsequent destabilization or lysis thereof.

Furthermore in the parenteral application of substances the problem of elimination has to be regarded in order to avoid an accumulation in the human or animal body and therefore toxic side effects.

Therefore pH-sensitive polymers should be provided which can be easily applied at concentrations in the range of for example 20 to 150 µg/ml and which are well chargeable and which therefore are suitable as carriers (complexes and conjugates) for bio-molecules, of natural or synthetic origin. They shall show good haemolytic properties in this range of concentration and in the range of pH 5.5 and below pH 6.5, while there shall be no membranolytic (haemolytic) effect at pH 7.4. Furthermore they shall not be effective against macrophage cell types by being toxic or being inhibiting. The polymers shall be eliminated well via the kidney and therefore be suitable also for parenteral applications.

The problem is solved by a pH-sensitive polymer which is a (meth)acrylic copolymer composed of
  20 to 65%, 25 to 65% by weight methacrylic acid units and 80 to 35%, 75 to 35 by weight units of $C_1$- to $C_{18}$-alkyl esters of (meth)acrylic acid, characterized in that it has a molecular weight in the range from 1 000 to 50 000 g/mol, and brings about at least 60% haemolysis at pH 5.5, and less than 5% haemolysis at pH 7.4, in a concentration of 150 µg/ml in a cytotoxicity test with human red blood cells.

Because poly(meth)acrylates—in contrast to other pharmaceutically used polymers—are not biologically degradable, the elimination must be effected by glomaerulous filtration via the kidney. However this process is restricted in respect to the molecular weight. An upper limit for molecules that can be secreted via the kidney is adopted with 50.000 g/mole (dalton). Surprisingly polymers with low molecular weights according to the present invention show higher haemolytic activities than those with higher molecular weights.

Implementation of the Invention (Meth)acrylate Copolymers
  The invention relates to a pH-sensitive polymer, in particular with membranolytic, haemolytic or cytotoxic properties at pH values below pH 6.5, which is a (meth)acrylate copolymer composed of
  20 to 65% by weight methacrylic acid units and 80 to 35% by weight units of $C_1$- to $C_{18}$-alkyl esters of (meth)acrylic acid, $C_1$- to $C_{18}$-alkyl esters of (meth)acrylic acid, in particular linear or branched $C_1$- to $C_{18}$-alkyl esters of (meth)acrylic acid, are, for example:
  methyl acrylate, ethyl acrylate, vinyl acrylate, propyl acrylate, butyl acrylate, hexyl acrylate, octyl acrylate, decyl acrylate, dodecyl acrylate, myristyl acrylate, lauryl acrylate, cetyl acrylate, stearyl acrylate, methyl methacrylate, ethyl methacrylate, propyl methacrylate, butyl methacrylate, isobutyl methacrylate, hexyl methacrylate, 2-ethylhexyl-(meth)acrylate, phenyl methacrylate, octyl methacrylate, decyl methacrylate, dodecyl methacrylate, myristyl methacrylate, lauryl methacrylate, cetyl methacrylate, stearyl methacrylate The ester components may be branched or cyclic.
Preference is given to the $C_1$- to $C_8$-alkyl esters of acrylic or methacrylic acid, in particular methyl methacrylate, ethyl methacrylate, butyl methacrylate, 2-ethylhexyl methacrylate, methyl acrylate, ethyl acrylate, butyl acrylate and 2-ethylhexyl acrylate.

As a rule, the stated contents add up to 100% by weight. However, it also possible, without this necessarily leading to an impairment or alteration in the essential properties, for small amounts in the range from 0 to 10, e.g. 0.1 to 5, or not more than 2.5, % by weight of other vinylically copolymerizable monomers, which are not necessarily (meth)acrylates, to be present, e.g. butyl acrylate, butyl methacrylate, methyl acrylate, hydroxyethyl methacrylate, hydroxyethyl acrylate, methacrylamide or styrene. Crosslinking monomers are not present as a rule.

(Meth)acrylate Copolymer Variants

Suitable and preferred for the purposes of the invention are (meth)acrylate copolymers composed of:
- 40 to 60, in particular 45 to 55, e.g. 50, % by weight methacrylic acid units and 60 to 40, in particular 55 to 45, e.g. 50, % by weight ethyl acrylate units (EUDRAGIT® L100-55 type).
- 40 to 60, in particular 45 to 55, e.g. 50, % by weight methacrylic acid units and 60 to 30, in particular 45 to 35, e.g. 50, % by weight ethyl acrylate units, and 2 to 20% by weight, e.g. 10% by weight, butyl methacrylate.
- 40 to 60, in particular 45 to 55, e.g. 50, % by weight methacrylic acid units and 60 to 40, in particular 55 to 45, e.g. 50, % by weight ethyl acrylate units, and 0.1 to 2% by weight of a $C_8$- to $C_{16}$-, preferably $C_8$-$C_{12}$-alkyl ester of acrylic or methacrylic acid, preferably dodecyl methacrylate. The copolymer can preferably be prepared in the presence of 5 to 15% by weight dodecyl mercaptan or 2 to 10% by weight 2-ethylhexyl thioglycolate and varies accordingly in its properties.
- 20 to 40, in particular 25 to 35, e.g. 30, % by weight methacrylic acid units, 25 to 45, in particular 30 to 40, e.g. 35, % by weight methyl methacrylate units, 25 to 45, in particular 30 to 40, e.g. 35, % by weight ethyl acrylate units.

As a rule, the stated contents add up to 100% by weight. However, it also possible, without this necessarily leading to an impairment or alteration in the essential properties, for small amounts in the range from 0 to 10, e.g. 0.1 to 5, or not more than 2.5, % by weight of other vinylically copolymerizable monomers, which are not necessarily (meth)acrylates, to be present. For example, butyl acrylate, butyl methacrylate, methyl acrylate, hydroxyethyl methacrylate, hydroxyethyl acrylate, methacrylamide or styrene may be mentioned.

Molecular Weight

The molecular weight can be determined for example by viscometry or gel exclusion chromatography (GPC). Viscometric values (limiting viscosity number) can be determined in chloroform or in DMF (dimethylformamide) at 23° C. and should preferably be in the range from 1 to 25, preferably 10 to 20, $n_{spec/c}$ (cm³/g). Viscosity numbers can be measured for example as specified in ISO 1628-6. The molecular weights according to this invention should be determined by viscosimetry according to DIN 1628-6, modified with DMF as a solvent. Viscosity numbers are correlated to the molecular weight (weight average, $M_w$) using poly methylmethacrylate (PMMA)-standards. The molecular weight (weight average) of the (meth)acrylate copolymer is in the range from 1 000 to 50 000 g/mol, preferably in the range from 5 000 to 40 000 g/mol, in particular in the range from 10 000 to 30 000 or most preferably in the range of 15 000 to 25 000.

The following table may be used as a guideline to calculate molecular weights from viscosity values (VZ) according to the general formula $VZ = 4,976 \cdot 10^{-3} \cdot M_w^{0,796}$:

| Viscosity number (VZ) | Molecular weight ($M_w$) |
|---|---|
| 1 | 780 |
| 3 | 3110 |

-continued

| Viscosity number (VZ) | Molecular weight ($M_w$) |
|---|---|
| 5 | 5910 |
| 10 | 14110 |
| 15 | 23490 |
| 20 | 33720 |
| 30 | 56110 |
| 50 | 106600 |

Haemolytic Effect

If the haemolytic activity (haemolysis) exceeds 5% there is said to be a cytotoxic effect. The haemolytic activity should be less than 5% at pH 7.4 and be high and be, for example, at least 30, at least 40, at least 50 or at least 60, % at pH 5.5. It is beneficial if this effect is reached with readily dosed copolymer concentrations of 20 to 300, preferably 50 to 250, in particular of 100 to 200, µg of copolymer/ml based on an erythrocyte concentration of $1 \times 10^8$ RBC/ml.

Most preferred are copolymer concentrations of 10 to 150, preferred from 15 to 110, in particular from 20 to 80 µg copolymer/ml.

In a cytotoxicity test with human red blood cells, the (meth) acrylic copolymer at a concentration of 150 µg/ml brings about at least 60%, preferably at least 80%, haemolysis at pH 5.5, and less than 5%, preferably less than 2.5, particularly preferably less than 1, % haemolysis at pH 7.4.

The cytotoxicity test with human red blood cells (erythrocytes) can be carried out by a method based on that of Murthy et al.: N. Murthy, J. R. Robichaud, D. A. Tirrell, P. S. Stayton, and S. Hoffman. The design and synthesis of polymers for eukaryotic membrane disruption. *J. Controlled Release*, 61: 137-143 (1999).

This entails human red blood cells (RBC) obtained from fresh blood being separated by centrifugation in the presence of K3 EDTA. The cells are in this case sedimented at 200 g and 4° C. for 5 min and subsequently washed three times by renewed centrifugation and taking up in phosphate-buffered saline (PBS buffer, 34 mM, pH 7.4, 0.9% NaCl weight/volume (75 mM)). The cell count in the resulting suspension can be determined using a haemocytometer.

The haemolysis test is carried out by adding the human red blood cells (RBC) in the particular medium to a copolymer suspension at a cell concentration of $1 \times 10^8$ RBC/ml. The mixture is incubated at 37° C. for 20 min.

Cytotoxic Effect on Macrophage-type Cells

In contrast to red blood cells, where the cytolysis presumably takes place mainly through an interaction of the copolymers with the outer cell membrane, the macrophage-like cell types are capable of active uptake of the copolymers, so that it must be assumed that other interactions may cause cytolysis in this case. The preferred (meth)acrylate copolymers are those showing low or zero cytolysis or toxicity in the MTT test or in the LDH test (lactate dehydrogenase test) with the mouse macrophage-like cell type J774A.1 (see Example 5). The cell line J774A.1 is available, for example, from the public collection of strains ATCC (America Type Culture Collection, Manassas, Va. 20108) under the No. TIB-67 (J774A.1 mouse cells; immortalized macrophage-like cells (not tumoral); see also: Ralph P et al. Lysozyme synthesis by established human and murine histiocytic lymphoma cell lines. J. Exp. Med. 143: 1528-1533, 1976 PubMed: 76192838.

MTT test (inhibition of cells of a macrophage-type cell line):

The calorimetric test detects living cells which reduce the yellow MTT dye (MTT=3-(4,5-dimethylthiazol-2-yl)-2,5-diphenyltetrazolium bromide) to a dark blue formazan product. The test is suitable for detecting cytotoxicity, cell proliferation and cell activation (see, for example, T. Mosmann. Rapid calorimetric assay for cellular growth and survival: Application to proliferation and cytotoxicity assays, *J. Immunol. Meth.* 65:55-63 (1983)).

The extent of killing of macrophage cells is indicated by the LDH released (N C. Phillips, L. Gagné, N. Ivanoff, g. Riveau. (1996) Vaccine 14(9), 898-904. The lactate dehydrogenase test for measuring the released LDH (see P. G. Cabaud and F. Wroblewski in Am J Clin Pathol (1958) 30, 234-236) can be carried out with commercially available test kits, e.g. Sigma kit (procedure No. 500).

Toxicity induced by the copolymers towards macrophage-like cells should be as low as possible at physiological (neutral) pH.

Preferred (meth)acrylate copolymers are therefore those which, at a concentration in the region of 0.03125 mg/ml, bring about in the MTT test with the macrophage-like cell type J774A.1 (ATCC TIB-67) a perventage-value of cell survival of at least 25%, preferably at least 60%, based on a 100% survival rate in the control experiment.

Preferred (meth)acrylate copolymers are therefore those which, at a concentration in the region of 0.03125 mg/ml, bring about in the LDH test with the macrophage-like cell type J774A.1 (ATCC TIB-67) a LDH release-value of not more than 40%, preferably not more than 20%, based on a 100% cytolysis (toxicity) in the control experiment.

Preparation of the pH-sensitive Polymers or (meth)acrylate Copolymers

The pH-sensitive polymers are prepared by free-radical polymerization of the monomers in the presence of polymerization initiators and molecular weight regulators by block, bead or emulsion polymerization and discharge of the polymer. Other preparation methods which are suitable in principle are also group transfer polymerization (GTP) or atom transfer radical polymerization (ATRP) (see, for example, Matyjaszewski, K. et al., Chem. Rev. 2001, 101, 2921-2990). The resulting polymer structures are random copolymers or block copolymers.

Preference is given to emulsion polymerization in the presence of 2 to 15% by weight molecular weight regulators, an emulsifier content in the range from 0.1 to 2% by weight, an amount of polymerization initiator in the range from 0.02 to 0.4% by weight and at temperatures from 65 to 90° C. Preference is given to an emulsifier mixture preferably composed of sodium lauryl sulphate, e.g. 0.1 to 0.5% by weight, and polyoxyethylene 20 sorbitan monooleate, e.g. 0.4 to 1.5% by weight. Particularly suitable initiators are sodium peroxidisulphate or ammonium peroxodisulphate. It is possible in this way to prepare, for example, a dispersion with a solids content of 20 to 40% by weight, and the copolymer can be isolate, preferably by spray drying or by coagulation and expelling the water in an extruder. The polymer is then dissolved, preferably in an organic solvent, purified, preferably by multiple dialysis against water, and dried, preferably freeze dried.

Examples of polymerization initiators which may be mentioned are: azo compounds such as 2,2'-azobis(isobutyronitrile) or 2,2'-azobis(2,4-dimethylvaleronitrile), redox systems such as, for example, the combination of tertiary amines with peroxides or, preferably, peroxides (concerning this, see, for example, H. Rauch-Puntigam, Th. Völker, "Acryl- und Methacrylverbindungen", Springer, Heidelberg, 1967 or Kirk-Othmer, Encyclopedia of Chemical Technology, Vol. 1, pages 386 et seq., J. Wiley, New York, 1978). Examples of suitable peroxide polymerization initiators are dilauroyl peroxide, tert-butyl peroctoate, tert-butyl perisononanoate, dicyclohexyl peroxydicarbonate, dibenzoyl peroxide or 2,2-bis(tert-butylperoxy)butane.

It is also possible and preferred for the polymerization to be carried out with a mixture of various polymerization initiators differing in half-life, for example, dilauroyl peroxide and 2,2-bis(tert-butylperoxy)butane, in order to keep the flow of free radicals constant during the polymerization and at different polymerization temperatures. The amounts of polymerization initiator employed are generally from 0.01 to a maximum of 1% by weight based on the monomer mixture.

The molecular weights of the copolymers (CP) are adjusted by polymerizing the monomer mixture in the presence of molecular weight regulators, such as, in particular, of the mercaptans known for this purpose, such as, for example, n-butyl mercaptan, n-dodecyl mercaptan, 2-mercaptoethanol or 2-ethylhexyl thioglycolate, generally employing the molecular weight regulators in amounts of 0.05 to 15% by weight based on the monomer mixture, preferably in amounts of 0.1 to 10% by weight and particularly preferably in amounts of 2 to 12% by weight of the monomer mixture (cf., for example, H. Rauch-Puntigam, Th. Völker, "Acryl- und Methacrylverbindunigen", Springer, Heidelberg, 1967; Houben-Weyl, Methoden der organischen Chemie, Vol. XIV/1, page 66, Georg Thieme, Stuttgart, 1961 or Kirk-Othmer, Encyclopedia of Chemical Technology, Vol. 1, pages 296 et seq., J. Wiley, New York, 1978). The molecular weight regulator preferably employed is n-dodecyl mercaptan or 2-ethylhexyl thioglycolate. Ethylhexyl thioglycolate has the advantage that the hydrophobicity of the (meth)acrylate copolymer can be influenced since the regulator is included in the molecule at the terminus. 5 to 15% by weight dodecyl mercaptan or 2 to 10% by weight 2-ethylhexyl thioglycolate are preferred amounts employed.

Conjugates/Complexes

The pH-sensitive polymer can be as intended in the form of a conjugate or complex with a pharmaceutically effective natural or synthetic biomolecule or an active pharmaceutical ingredient. The conjugate or complex can be prepared reversibly or irreversibly covalently by chemical linkage or through secondary valencies via Van der Waals forces, ionic bonds, hydrophobic linkage.

Uses

The pH-sensitive polymers can be used as carriers, conjugates/complexes for natural or synthetic biomolecules or active pharmaceutical ingredients which are to be released inside cells via uptake into endosomes and subsequent destabilization or lysis thereof.

The pH-sensitive polymers can be used for complexation or as conjugated with lipids, proteins, peptides, nucleic acids (DNA ad RNA), in particular oligonucleotides, antisense DNA or antisense RNA, plasmid DNA, nucleotides, hormones, toxins, immunotoxins, antibodies or fragments thereof or active pharmaceutical ingredients. The complexation or conjugate formation can take place reversibly or irreversibly covalently by chemical linkage or through secondary valencies via Van der Waals forces, ionic bonds, hydrophobic linkage. The resulting complex can be used as active ingredient for producing a drug form, in particular a dermal, transdermal, parenteral, nasal, pulmonary, vaginal or oral drug form.

The pH-sensitive polymers and the conjugates may, where appropriate, be a constituent of microparticles, nanoparticles, liposomes, emulsions and/or lipid vesicles.

The said use as carrier, conjugate/complex is possible and preferred for active pharmaceutical ingredients from the active ingredient classes of analgesics, antiallergics, antirheumatics, antibiotics, antiinfectives, antiparkinson agents, antipsoriatics, antitumour agents, dermatologicals, gout remedies, immunoregulators, gastrointestinal agents, neurotropic agents, ophthalmologicals, cytostatics.

Possible disorders:

cancer, infections (including HIV), cardiovascular disorders (e.g. arteriosclerosis), arthritis, neurodegenerative disorders (Parkinsonism, multiple sclerosis, Alzheimer's), genetically related enzyme-deficiency disorders, hepatitis B and C, mucoviscidosis, hypercholesteraemia, Down's syndrome, muscular dystrophy, autoimmune diseases, shingles and herpes, psoriasis, CMV retinitis, Crohn's disease, ulcerative colitis, diabetes.

The medicinal substances employed for the purpose of the invention are intended to be used on or in the human or animal body in order 1. to cure, alleviate, prevent or diagnose disorders, conditions, physical damage or pathological symptoms.
2. to reveal the condition, the status or the functions of the body or mental states.
3. to replace active substances or body fluids produced by the human or animal body.
4. to ward off, to eliminate or to render harmless pathogens, parasites or exogenous substances, or
5. to influence the condition, the status or the functions of the body or mental states.

Medicinal substances in use are to be found in reference works such as, for example, the Rote Liste or the Merck Index.

Particular mention should be made of the active ingredients amphotericin B, cytosine arabonoside Adriamycin. The liposomal form of adriamycin could also be a good model since its fast release in endosomes could be used to overcome multidrug resistance. Other active ingredients of interest could be antisense oligonucleotides, plasmid DNA and peptides (leuprolide, calcitonin etc.).

The drug form can be used for example for the therapy of tumours, cardiovascular disorders or rheumatoid arthritis. Gene therapy of genetic disorders or prophylactic therapy of such disorders with the aid of the pH-sensitive polymers according to the invention as ingredient of appropriate drug forms is likewise conceivable in future. Compared with viral systems for transferring nucleic acids into living cells, non-viral systems have the general advantage that they can be prepared more easily, no replication of the vector is involved, and that the risk of immunological reactions is lower.

Modifications of the Properties a) Influencing the Conformation by Binding Other Molecules The properties, e.g. the toxic or membranolytic activity, of the (meth)acrylate copolymers on red blood cells and/or macrophage-type cells or the physical properties thereof can be modified by covalent or secondary valency coupling with other molecules, in particular conformation-altering agents, e.g. dyes, in particular hydrophobic dyes, e.g. with rhodamine B. Suitable coupling methods for carboxyl group-containing (meth)acrylate copolymers are known to the skilled person.

It is possible to obtain for example a (meth)acrylate copolymer composed of
  25 to 65% by weight methacrylic acid units and 75 to 35% by weight units of $C_1$- to $C_{12}$-alkyl esters of (meth)acrylic acid, which is modified or coupled with a dye, preferably with a hydrophobic dye, in particular with rhodamine B.

Preference is given to a (meth)acrylate copolymer composed of
  40 to 60% by weight methacrylic acid units and 60 to 40% by weight ethyl acrylate units, which is modified with a dye, preferably with an in particular hydrophobic dye, in particular with rhodamine B.

Preference is given to a theoretically determined coupling ratio in which 5 to 100%, preferably 5 to 20%, of the copolymer molecules are coupled with a dye molecule.

The coupling has the advantage for example that the solubility characteristics can be modified. It is possible, for example, to achieve a steep rise in insolubility in the region below pH 6.5, e.g. in the range from pH 6.0 to pH 5.0 (see Example 6).

b) Production of Complexes by Intermolecular Crosslinking

The carboxyl groups of the (meth)acrylate copolymers are chemically reactive and are suitable for the modification with the aim of producing complexes by intermolecular crosslinking. Thus, for example, SH groups can be introduced relatively easily into the (meth)acrylate copolymers by chemical modification with $NH_2$—$CH_2$—$CH_2$—$SH$.

It is likewise easy to introduce SH groups into DNA and RNA, in particular oligonucleotides, antisense DNA or antisense RNA, via the 5'- and 3'-terminal OH groups of nucleic acids by means of $COOH$—$CH_2$—$CH_2$—$SH$.

SH-modified (meth)acrylate copolymers and SH-modified nucleic acids can be crosslinked by forming S—S bridges to give complexes. The increase in the molecular weight and the reduced solubility makes the complexes available in granule form in particular to phagocytotic cells, which may be advantageous in the treatment of certain pathological states such as, for example, (auto)immune diseases.

Reduction of the disulfide bridge in vivo would release the active form of the carried molecule. The complexes could also be internalised by other cell types after grafting appropriate targeting ligands.

The polymers according to the invention are employed in combination with active ingredients and form a drug delivery system which is particulate as a rule. It is possible for this purpose to link the active ingredient to the polymer via a biodegradable spacer. However, preference is also given to conjugates/complexes with cationic low molecular weight or polymeric substances and pharmalogically active agents. Mention should be made of cationic lipids such as Lipofectin, polylysine, polyethyleneimine, polyamino(meth)acrylate or spermine and spermidines and derivatives thereof. This complex may also be a cationic or anionic liposome. Polymer and active agent may also be incapsulated in or bound to a cationic, anionic or neutral liposome.

The complexing agents which are known per se may display action-enhancing effects in a variety of ways (e.g. polyethyleneimine).

Further constituents of the complexes may be hydrophilic polymers (polyethylene glycol, polyvinylpyrrolidone, polylactides, polyglycolides, polysaccharides and derivatives thereof). These substances protect the active ingredients from interactions with constituents of the blood and prolong the circulation in the blood.

Targeting ligands, such as antibodies against cell-specific antigens can be used for cell-specific targeting.

The particulate release systems are produced by conventional techniques, e.g. by direct complexation in solution, drying of lipid-containing solutions and redispersion in water, where appropriate using ultrasound or homogenization.

Ingredient of a drug form which corresponds to the usual technique of the intended use and, permits a safe under tolerated therapy. The stability can be extended by freeze- or spray-drying the drug forms.

EXAMPLES

1. Copolymers of Examples 1 to 7

Copolymer A:
  Copolymer of
  50% by weight methacrylic acid and
  50% by weight methyl methacrylate.
  Weight average molecular weight=$M_w$ about 25 000.

Copolymer B:
  Copolymer of
  50% by weight methacrylic acid and
  50% by weight ethyl acrylate.
  Weight average molecular weight=$M_w$ about 25 000.

Copolymer C:
  Copolymer of
  30% by weight methacrylic acid,
  35% by weight ethyl acrylate and
  35% by weight methyl acrylate
  Weight average molecular weight=$M_w$ about 25 000.

Copolymer D:
  Copolymer of
  30% by weight methacrylic acid,
  70% by weight methyl methacrylate.
  Weight average molecular weight=$M_w$ about 25 000.

Copolymer E (Not According to the Invention)
  Copolymer of
  10% by weight methacrylic acid,
  45% by weight methyl methacrylate and
  45% by weight methyl acrylate
  Weight average molecular weight=$M_w$ about 25 000.

Copolymer L-100 (EUDRAGIT® L, Not According to the Invention)
  Copolymer of
  50% by weight methacrylic acid and
  50% by weight methyl methacrylate.
  Weight average molecular weight=$M_w$ about 100 000.

Copolymer L-100-55 (EUDRAGIT® L100-55, Not According to the Invention)
  Copolymer of
  50% by weight methacrylic acid and
  50% by weight ethyl acrylate.
  Weight average molecular weight=$M_w$ about 250 000.

Copolymer S-100 (EUDRAGIT® S100, Not According to the Invention)
  Copolymer of
  30% by weight methacrylic acid and
  70% by weight methyl methacrylate.
  Weight average molecular weight=$M_w$ about 100 000.

Example 1 pH Transition Ranges (Soluble to Insoluble)

The intention was to investigate, by measuring the scattered light at 37° C. at pH values from 3.0 to 7.5 in phosphate buffer, the pH ranges in which the copolymers are present in insoluble form. The intensity of light scattering increases as the polymer precipitates.

The results are shown in Table 1 below

TABLE 1

| Copolymer | Methacrylic acid [wt %] | Methyl methacrylate [wt %] | Ethyl acrylate [wt %] | Methyl acrylate [wt %] | Mw × 10$^3$ [mol/g] | pH range in which the copolymer precipitates |
|---|---|---|---|---|---|---|
| A | 50 | 50 | — | — | 25 | 3.8–4.5 |
| B | 50 | — | 50 | — | 25 | 4.7–5.1 |
| C | 30 | — | 35 | 35 | 25 | 5.0–5.6 |
| D | 30 | 70 | — | — | 25 | 4.8–5.3 |
| E | 10 | 45 | — | 45 | 25 | 4.5–7.0 |
| L-100 | 50 | 50 | — | — | 100 | 3.7–4.3 |
| L-100-55 | 50 | — | 50 | — | 250 | 4.6–5.0 |
| S-100 | 30 | 70 | — | — | 100 | 4.7–5.2 |

Results:
The (meth)acrylate copolymers, except copolymer E, show relatively narrow transition ranges of from 0.4 to 0.7 pH units.

Copolymer E appears, because of its low content of 10% by weight monomers with carboxyl group residues, to have a wider pH transition range of 2.5 pH units.

The molecular weight appears to have virtually no effect on the solubility characteristics of the copolymers.

Example 2

Concentration-dependent Haemolytic Activity at pH 7.4

The cytotoxicity test with human red blood cells was carried out by a method based on that of Murthy et al. (N. Murthy, J. R. Robichaud, D. A. Tirrell, P. S. Stayton, and S. Hoffman. The design and synthesis of polymers for eukaryotic membrane disruption. *J. Controlled Release*, 61: 137-143 (1999)).

This entails human red blood cells (RBC) being separated by centrifugation in the presence of K3 EDTA. The cells are in this case sedimented at 200 g and 4° C. for 5 min and subsequently washed three times by renewed centrifugation and taking up in phosphate-buffered saline (PBS buffer, 34 mM, pH 7.4, 0.9% NaCl weight/volume (75 mM)). The cell count in the resulting suspension can be determined using a haemocytometer.

The haemolysis test is carried out by adding the human red blood cells (RBC) in the particular medium to a copolymer suspension at a cell concentration of $1 \times 10^8$ RBC/ml. The mixture is incubated at 37° C. for 20 minutes. The degree of haemolysis was measured by spectrometric determination of the haemoglobin released from lysed cells in the centrifugation supernatant at 541 nm.

The results are shown in Table 2 below.

| Copolymer | Mw × 10³ [mol/g] | Haemolytic activity [%] at pH 7.4 with a copolymer concentration in [µg/ml] | | | | |
|---|---|---|---|---|---|---|
| | | 150 | 250 | 500 | 2 500 | 10 000 |
| A | 25 | <5 | <5 | <5 | <5 | <5 |
| B | 25 | <5 | 5 | 8 | 25 | 100 |
| C | 25 | <5 | <5 | 5 | 100 | 100 |
| D | 25 | <5 | <5 | <5 | 100 | 100 |
| E | 25 | <5 | <5 | <5 | 12 | 20 |
| L-100 | 100 | <5 | <5 | <5 | <5 | <5 |
| L-100-55 | 250 | <5 | <5 | <5 | <5 | 30 |
| S-100 | 100 | <5 | <5 | <5 | <5 | <5 |

Result:

Copolymers B and C show a haemolytic activity of 5% or more (toxicity threshold) at pH 7.4 at 500 µg/ml and upwards. Copolymers B, C, D and E show haemolytic activities of more than 5% at 2.500 µg/ml. The haemolytic activity of copolymer B is in this case less than that of C and D.

Copolymers A, L-100, L-100-55 and S-100 have no haemolytic activity even at high concentrations up to 10 000 µg/ml. Copolymer L-100-55, which is identical to copolymer B apart from its molecular weight, and coplymer E show a slight haemolytic activity at 10 000 µg/ml.

Copolymers A and B have an identical 50% by weight methacrylic acid content and differ only in the comonomer—respectively methyl methacrylate and ethyl acrylate. The somewhat more hydrophobic copolymer B is haemolytic even at 250 µg/ml. By contrast, copolymer A is not haemolytic even at 10 000 µg/ml.

Example 3

Haemolytic Effect of Copolymers B and C in Different Concentrations at pH 5.0 and pH 5.5

The results are shown in Table 3 below.

TABLE 3

| Copolymer | pH | Haemolytic activity [%] at a copolymer concentration in [µg/ml] | | | | |
|---|---|---|---|---|---|---|
| | | 25 | 50 | 100 | 150 | 250 |
| B | 5.0 | 10 | 80 | 80 | 80 | 80 |
| B | 5.5 | 50 | 90 | 95 | 90 | 90 |
| L-100-55 | 5.0 | <5 | 80 | 80 | 80 | 80 |
| L-100-55 | 5.5 | 5 | 55 | 75 | 90 | 90 |
| C | 5.0 | <5 | <5 | 10 | 60 | 80 |
| C | 5.5 | 5 | 50 | 80 | 85 | 85 |

Result:

Copolymer B is more haemolytic than copolymer C at pH 5.0 and at pH 5.5, especially at low concentrations of 25 and 50 µg/ml. Both copolymers are very active at pH 5.5 and 150 µg/ml.

Copolymer L-100-55 differs from copolymer B by its higher molecular weight. The haemolytic activity of copolymer B is higher than that of copolymer L-100-55 at pH 5.0 and pH 5.5 at 25 and 50 µg/ml as well as at pH 5.5 and 100 µg/ml.

Example 4

Haemolytic Effect at a Copolymer Concentration of 150 µg/ml and Various pH Values The results are shown in Table 4 below.

TABLE 4

| Copolymer | Mw × 10³ [mol/g] | Haemolytic activity [%] with a copolymer concentration of 150 [µg/ml] | | | | |
|---|---|---|---|---|---|---|
| | | pH 5.5 | pH 6.0 | pH 6.5 | pH 7.0 | pH 7.5 |
| A | 25 | <5 | <5 | <5 | <5 | <5 |
| B | 25 | 80 | 55 | <5 | <5 | <5 |
| C | 25 | 90 | 55 | <5 | <5 | <5 |
| D | 25 | <5 | <5 | <5 | <5 | <5 |
| E | 25 | <5 | <5 | <5 | <5 | <5 |
| L-100 | 100 | <5 | <5 | <5 | <5 | <5 |
| L-100-55 | 250 | 95 | 80 | <5 | <5 | <5 |
| S-100 | 100 | <5 | <5 | <5 | <5 | <5 |

Result:

Copolymers B, C and L 100-55 show strong haemolytic activity in a concentration of 150 µg/ml in the pH range from 5.5 to 6.0. All the copolymers contain ethyl acrylate as comonomer. The Mw of L 100-55 is too high for applications, however.

Example 5

The intention was to investigate the effect of the copolymers on macrophage cell types. In contrast to red blood cells, with which cytolysis presumably takes place mainly through an interaction of the copolymers with the outer cell membrane, macrophage cell types are capable of active uptake of the copolymers, so that it must be assumed that other interactions are able to cause cytolysis or other toxic effects in this case. Since the determination of cytolysis or other toxic effects is relatively inexact, two test systems are combined: the MTT assay to access cell proliferation and the LDH assay to access cellular necrosis (MTT test for surviving cells and the LDH test for killed cells).

MTT Test

MTT test (inhibition of cell proliferation of a macrophage-type cell line).

The calorimetric test detects living cells which reduce the yellow MTT dye to a dark blue formazan product. The test is suitable for detecting cytotoxicity, cell proliferation and cell activation (see, for example, T. Mosmann. Rapid calorimetric assay for cellular growth and survival: Application to proliferation and cytotoxicity assays, *J. Immunol. Meth.* 65: 55-63 (1983)).

J 774 mouse macrophage-type cells are suspended in DMEM medium containing 10% vol/vol foetal calf serum (pretreated at 56° C., 30 min) and 100 U/ml penicillin G and 100 µg/ml streptomycin. The cells are distributed in 100 µl portions containing $5 \times 10^3$ cells in a microtiter plate with 96 wells and incubated under an $H_2O$-saturated atmosphere containing 5% $CO_2$ at 37° C. for 24 h. 20 µl of sterile copolymer solution are added, and serial dilutions from 0.5 to 0.003125 mg/ml are carried out (controls receive phosphate buffer without copolymer). Incubation is then continued for 48 h.

10 µg of a sterile MTT solution (MTT=3-(4,5-dimethylthiazol-2-yl)-2,5-diphenyltetrazolium bromide) in phosphate buffer (5 mg/ml) are put in each well and incubated at 37° C. for a further 3 h. Then 100 µl of a 10% weight/volume sodium dodecyl sulphate solution (SDS) in 0.01 M HCl are added in order to solubilize reduced MTT. The absorption at 570 nm is measured in a spectrometer after 24 h and is evaluated in relation to a 100% survival rate in the control experiment without addition of copolymer.

LDH Test

The colorimetric test detects lactate dehydrogenase (LDH) activity released by killed cells. The test is carried out in analogy to the MTT test with J774 cells in microtiter plates. After incubation for 48 h, 4 µl portions of the supernatant are tested for LDH activity with a commercially available LDH test kit. Evaluation takes place in relation to 100% cytolysis (toxicity) in the control experiment without addition of copolymer. The 100% value is in this case determined after incubation of a cell aliquot in the presence of Triton X-100 for complete cytolysis.

The results are shown in Table 5 below.

TABLE 5

| Co-polymer | MAA | MMA | EA | MA | MTT test % cell survival | | LDH test % LDH released | |
|---|---|---|---|---|---|---|---|---|
| | | | | | 0.03125 [mg/ml] | 0.5 [mg/ml] | 0.03125 [mg/ml] | 0.5 [mg/ml] |
| A | 50 | 50 | — | — | 90 | 100 | <5 | <5 |
| B | 50 | — | 50 | — | 30 | 20 | 35 | 40 |
| C | 30 | — | 35 | 35 | 100 | 80 | <5 | 15 |
| D | 30 | 70 | — | — | 100 | 100 | <5 | <5 |
| E | 10 | 45 | — | 45 | 100 | <5 | <5 | 40 |

MAA = [wt %] methacrylic acid
MMA = [wt %] methyl methacrylate
EA = [wt %] ethyl acrylate
MA = [wt %] methyl acrylate Result:

The measurements obtained in the MTT test and LDH test agree qualitatively. Copolymer B is the most toxic for J774 even in low concentration. No toxic effect was detectable for copolymers A and D. Copolymer E, which causes limited haemolysis of red blood cells in Example 4, proves to be toxic for J774 cells in a concentration of 0.5 mg/ml. Copolymer C proves to be slightly toxic for the J774 cells in a concentration of 0.5 mg/ml.

Example 6 pH-dependent Conformational Change (Transition) of Copolymers A to E

Pyrene Fluorescence

The fluorescent dye pyrene can be used to follow the transition of pH-sensitive polymers at different pH values (see, for example: K. Kalyanasundaram and J. K. Thomas. Environmental effects on vibronic band intensities in pyrene monomer fluorescence and their application in studies of micellar systems. *J. Am. Chem. Soc.* 99:2039-2044 (1977)).

The transitions from the hydrophilic coiled structures (coil) to hydrophobic globule structures are associated with a decrease in the ratio of the first (372 nm) and the third (383 nm) peaks the emission spectrum ($I_1/I_3$ ratio). For the measurement, pyrene is simply added to the copolymer solution.

The results are shown in Table 6 below.

TABLE 6

| Co-polymer | MAA | MMA | EA | MA | Pyrene emission ($I_{372\ nm}/I_{383\ nm}$) | | | |
|---|---|---|---|---|---|---|---|---|
| | | | | | pH 5.5 | pH 6.0 | pH 6.5 | pH 7.4 |
| A | 50 | 50 | — | — | 1.32 | 1.39 | 1.45 | 1.52 |
| B | 50 | — | 50 | — | 1.25 | 1.39 | 1.46 | 1.48 |
| C | 30 | — | 35 | 35 | 1.27 | 1.31 | 1.35 | 1.46 |
| D | 30 | 70 | — | — | 1.22 | 1.23 | 1.27 | 1.36 |
| E | 10 | 45 | — | 45 | 1.27 | 1.26 | 1.26 | 1.26 |

Result:

Copolymers A and B (50% by weight methacrylic acid) show the most pronounced transition from pH 7.4 to pH 5.5, followed by copolymers C and D (30% by weight methacrylic acid). Copolymer E (10% by weight methacrylic acid) shows virtually no transition behaviour. The transition behaviour appears to correlate with the methacrylic acid content of the copolymers but not with the haemolytic activity of the copolymers (see Examples 2 and 4).

Example 7

Coupling of Copolymer B with the Dye Lissamine® (Rhodamine B)

The test is carried out as described in K. Abdellaoui, M. Boustta, M. Vert, H. Morjani, M. Manfait. (1998) Eur J Pharm Sci 6, 61-73, with the following modifications. The carboxyl group-activator N-ethoxycarbonyl-2-ethoxy-1,2-dihydroquinoline (EEDQ) was replaced by 1,3-diisopropylcarbodiimide (DIPC). 4-(Dimethylamino)pyridine (DMAP) and triethylamine are added in catalytic amounts. The reaction is carried out for 4 days.

250 mg of copolymer B were dissolved in 1 ml of previously distilled tetrahydrofuran (THF). Then 0.5 mg/ml ($3 \times 10^{-3}$ mmol) 1,3-diisopropylcarbodiimide (DIPC) were added to activate the carboxyl groups. After 30 min, catalytic amounts of triethylamine and 4-(dimethylamino)pyridine and Lissamine® rhodamine B ethylenediamine (1 mg/ml, $1.5 \times 10^{-3}$ mmol), dissolved in anhydrous N,N-dimethylformamide. The reaction mixture was incubated at room temperature in the dark under argon for 96 h.

The reaction mixture was passed through a 0.2 µm filter to remove the precipitated DIPC by product. The THF present was stripped off in vacuo. To the crude product still containing THF a mixture of chloroform/methanol (85/15 vol/vol) was added and the solution was eluted on a silica gel column to eliminate free rhodamine. The elution process in this case was monitored by thin-layer chromatography. The appropriate fractions were combined and the solvent was stripped off in vacuo. The residue was taken up in THF and dialysed against water/methanol (50/50) using a 3 500 dalton membrane for 3 days in order to remove residues of noncovalently bound rhodamine B. The dialysis was then continued against phosphate buffer pH 9 for 2 days and against distilled water for a further 2 days. The resulting product was freeze dried for 72 h.

The rhodamine B content in the copolymer was determined by spectrofluorometry in methanol at room temperature ($\lambda_{exc}$=560 nm, $\lambda_{em}$=580 nm).

The yield of crimson-coloured copolymer was 83%. The, rhodamine B binding was found to be 0.04 mol %, which means that theoretically one in 9 copolymer molecules is coupled to a rhodamine molecule.

It was intended to test the solubility characteristics at various, pH values, comparing with copolymer not coupled to rhodamine B.

The results are shown in Table 7 below.

TABLE 7

|  | Insolubility (precipitation) in [%] at pH | | | | | |
| --- | --- | --- | --- | --- | --- | --- |
| pH | 4.2 | 4.5 | 5.3 | 5.6 | 6.0 | 7.0 |
| Copolymer B | 100 | 70 | 5 | <5 | <5 | <5 |
| Copolymer B rhodamine B | 70 | 70 | 100 | 10 | <5 | <5 |

Result:

Rhodamine coupling to copolymer B brings about a marked change in the solubility characteristics. There is a steep rise from about pH 5.6 to 100% insolubility at pH 5.3. In contrast to this, the uncoupled copolymer B does not show 100% insolubility until the pH is 4.2. The rise in this region takes place distinctly less steeply from about pH 5.3.

Example 8

Preparation processes: one example is given for each of preparation processes 1 and 2. The proportionate amounts can be varied as indicated in the table on page 38.

The weight average molecular weight (Mw) can be calculated approximately from the measurements for the viscosity $n_{spec/c}$ (cm$^3$/g) relative to the viscosity of polymethyl methacrylate (PMMA) at 25° C. in DMF (dimethylformamide). The following empirically found formula is used for this purpose:

$$M = \left(\frac{[\eta]}{4.976 \cdot 10^{-3}}\right)^{\frac{1}{0.796}}$$

Preparation Process 1

1 430 g of distilled water, 3.78 g of sodium lauryl sulphate, 12.6 g of polyoxyethylene 20 sorbitan monooleate and 1.26 g of ammonium peroxodisulphate, dissolved in 20 g of distilled water, were introduced into a reaction vessel with a capacity of 2 l, equipped with reflux condenser, stirrer and feed vessel. At 81° C., a monomer mixture consisting of:
270 g of ethyl acrylate
270 g of methacrylic acid
27 g of 2-ethylhexyl thioglycolate
was metered into a solution over the course of 2.5 hours.

After the feed was complete, the mixture was kept at 81° C. for a further 2 hours, a mixture of 0.176 g of SE-2MC silicone antifoam emulsion and 10 g of distilled water was added, and 95.42 g of distilled water was stripped off in vacuo at about 300 mbar, and cooled to room temperature. The dispersion has a solids content of 30%.

Preparation Process 2

774 g of distilled water, 1.092 g of sodium lauryl sulphate and 1.4 g of sodium peroxodisulphate, dissolved in 10 g of distilled water, were introduced into a reaction vessel with a capacity of 2 l, equipped with reflux condenser, stirrer and feed vessel. At 75° C., an emulsion consisting of:
390 g of methyl acrylate
150 g of methyl methacrylate
60 g of methacrylic acid
1.008 g of sodium lauryl sulphate
7 g of polyoxyethylene 20 sorbitan monooleate
30 g of 2-ethylhexyl thioglycolate
820.99 g of distilled water
was metered into this solution over the course of 4 hours.

After the feed was complete, the mixture was kept at 75° C. for a further 2 hours, a mixture of 0.21 g of SE-2MC silicone antifoam emulsion and 10 g of distilled water was added, and 120 g of distilled water were stripped off under about 300 mbar, and cooled to room temperature. The dispersion has a solids content of 30%.

| Batch No. | Polymer composition (% by wt) | Regulator (parts) | Preparation process | Polym. temp. (° C.) | Emulsifier (parts) | Initiator (parts) | Solids content (%) | $n_{spec/c}$ (cm$^3$/g) | calc. Mw**** |
| --- | --- | --- | --- | --- | --- | --- | --- | --- | --- |
| 1 | A-B-C = 65-25-10 | 5 G | 2 | 75 | 0.15 I 0.5 K | 0.1 L | 30 | 10 | 14114 |
| 2* | B-C = 51-49 | 3 G | 2 | 80 | 0.125 I | 0.125 J | 40 | 17.7 | 28918 |
| 3 | D-C = 50-50 | 5 G | 1 | 81 | 0.3 I 1 K | 0.1 J | 30 | 13 | 19624 |
| 4** | B-C = 70.7-29.3 | 5 G | 2 | 80 | 0.125 I | 0.13 J | 40 | 10.2 | 14469 |
| 5 | A-D-C = 40-30-30 | 5 G | 2 | 75 | 0.15 I | 0.1 L | 30 | 11.7 | 17191 |
| 6 | D-C = 50-50 | 5 G | 1 | 81 | 0.3 I 1 K | 0.1 J | 30 | 13.7 | 20961 |
| 7 | D-E-C = 49.5-0.5-50 | 5 G | 1 | 81 | 0.3 I 1 K | 0.1 J | 30 | 13.9 | 21346 |
| 8 | D-E-C = 49-1-50 | 5 G | 1 | 81 | 0.3 I 1 K | 0.1 J | 30 | 13.9 | 21346 |
| 9 | D-E-C = 49.5-0.5-50 | 10 H | 1 | 81 | 0.3 I 1 K | 0.1 J | 30 | 12.3 | 18306 |
| 10 | D-E-C = 49-1-50 | 10 H | 1 | 81 | 0.3 I 1 K | 0.1 J | 30 | 12 | 17747 |

-continued

| Batch No. | Polymer composition (% by wt) | Regulator (parts) | Preparation process | Polym. temp. (°C.) | Emulsifier (parts) | Initiator (parts) | Solids content (%) | $n_{spec/c}$ (cm³/g) | calc. Mw**** |
|---|---|---|---|---|---|---|---|---|---|
| 11 | D-F-C = 40-10-50 | 10 H | 1 | 81 | 0.3 I<br>1 K | 0.1 J | 30 | 12 | 17747 |

*Final polymerization with 0.01 part of sodium disulphite, 0.0007 part of iron(II) sulphate, 0.05 part of ammonium peroxodisulphate
**Final polymerization with 0.01 part of sodium disulphite, 0.0007 part of iron(II) sulphate, 0.055 part of ammonium peroxodisulphate
****calculated molecular weight (Mw) relative to PMMA at 25° C./DMF $$M = \left(\frac{[\eta]}{4.976 \cdot 10^{-3}}\right)^{\frac{1}{0.796}}$$

A = methyl acrylate
B = methyl methacrylate
C = methacrylic acid
D = ethyl acrylate
E = dodecyl methacrylate
F = butyl methacrylate
G = 2-ethylhexyl thioglycolate
H = dodecyl mercaptan
I = sodium lauryl sulphate
J = ammonium peroxodisulphate
K = polyoxyethylene 20 sorbitan monooleate
L = sodium peroxodisulphate

The invention claimed is:

1. A pH-sensitive polymer comprising:
   25 to 65% by weight of methacrylic acid units, and
   60 to 35% by weight of units of ethyl acrylate;
   wherein the pH-sensitive polymer has a molecular weight in the range from 1,000 to 50,000 g/mol,
   and
   brings about at least 60% haemolysis at pH 5.5, and less than 5% haemolysis at pH 7.4, at a concentration of 150 μg/ml in a cytotoxicity test with human red blood cells.

2. The pH-sensitive polymer according to claim 1,
   wherein the pH-sensitive polymer comprises:
   40 to 60% by weight of methacrylic acid units and
   60 to 40% by weight of ethyl acrylate units.

3. The pH-sensitive polymer according to claim 1,
   wherein the pH-sensitive polymer comprises
   30 to 50% by weight of methacrylic acid units,
   and
   35 to 50% by weight of ethyl acrylate units.

4. The pH-sensitive polymer according to claim 1,
   wherein the pH-sensitive polymer essentially consists of:
   50 wt. % methacrylic acid and 50 wt. % ethylacrylate; or
   30 wt. % methacrylic acid, 35 wt. % ethylacrylate, and 35 wt. % methylacrylate.

5. The pH-sensitive polymer according to claim 1,
   wherein the pH-sensitive polymer does not contain transition metal complexes.

6. The pH-sensitive polymer according to claim 1, which brings about in a MTT test with the macrophage-like cell type J774A.1 (ATCC TIB-67) a percentage value of cell survival of at least 25% when the concentration of pH-sensitive polymer is 0.03125 mg/ml.

7. The pH-sensitive polymer according to claim 6, which brings about in a LDH test with the macrophage-like cell type J774A.1 (ATCC TIB-67) a LDH release value of not more than 40% when the concentration of pH-sensitive polymer is 0.03125 mg/ml.

8. A pH-sensitive polymer according to claim 1, further comprising a pharmaceutically effective natural or synthetic biomolecule or an active pharmaceutical ingredient.

9. The pH-sensitive polymer according to claim 8, wherein the pH-sensitive polymer is coupled to a conformation-altering agent.

10. The pH-sensitive polymer according to claim 8, wherein the pH-sensitive polymer is a constituent of a complex crosslinked via nucleic acids after chemical modification.

11. A process for preparing a pH-sensitive polymer according to claim 1, the process comprising:
    free-radically polymerizing 25 to 65% by weight of methacrylic acid monomer units with 60 to 35% by weight of monomer units of ethylacrylate in the presence of polymerization initiators and molecular weight regulators by block polymerization, bead polymerization, emulsion polymerization, group transfer polymerization (GTP), or atom transfer radical polymerization (ATRP) to form the polymer, and optionally:
    discharging the polymer,
    dissolving the polymer,
    purifying the polymer and/or
    drying the polymer.

12. The process according to claim 11, wherein the molecular weight regulator is dodecyl mercaptan and/or 2-ethylhexyl thioglycolate.

13. The pH-sensitive polymer of claim 1 which is produced by free radical polymerization of said monomers in the presence of a polymerization initiator and molecular weight regulator by block, bead or emulsion polymerization.

14. The pH-sensitive polymer of claim 1 which is not produced by catalytic chain polymerization (CCT), group transfer polymerization (GTP) or by atom transfer radical polymerization (ATRP).

15. A pH-sensitive polymer according to claim 1, wherein said pH-sensitive polymer is produced by polymerizing methacrylic acid and ethylacrylate in the presence of a molecular weight regulator which incorporates on a terminal of said polymer.

16. The pH-sensitive polymer of claim 15, which is produced by polymerizing a monomer mixture of methacrylic acid and ethylacrylate in the presence of 5 to 15% of n-dodecyl mercaptan by weight based on the weight of the monomer mixture.

17. The pH-sensitive polymer of claim 15, which is produced by polymerizing a monomer mixture of methacrylic acid and ethylacrylate in the presence of 5 to 10% of 2-ethylhexyl thioglycolate by weight based on the weight of the monomer mixture.

* * * * *